United States Patent [19]

Fricker

[11] Patent Number: 6,043,023
[45] Date of Patent: Mar. 28, 2000

[54] METHOD OF IDENTIFICATION OF NOVEL SUBSTRATES

[75] Inventor: Lloyd D. Fricker, New Rochelle, N.Y.

[73] Assignee: Albert Einstein College of Medicine of Yeshiva University, Bronx, N.Y.

[21] Appl. No.: 08/801,647

[22] Filed: Feb. 18, 1997

[51] Int. Cl.[7] ............................................. C12Q 1/00
[52] U.S. Cl. .............................. 435/4; 435/7.1; 435/7.6; 435/18
[58] Field of Search ................................. 435/4, 7.1, 7.6, 435/18

[56] References Cited

U.S. PATENT DOCUMENTS 5,624,818   4/1997   Eisenman et al. ..................... 435/69.1

OTHER PUBLICATIONS

Hibi, M. et al., "Indentification of an oncoprotein–and UV–responsive protein kinase that binds and potentiates the c–Jun activation domain," Genes and Development (Nov. 1993), vol. 7, No. 11, pp. 2135–2148.

McLaughlin, M.M. et al. "Indentification of mitogen–activated protein (MAP) kinase–activated protein kinase–3, a novel substrate of CSPB p38 MAP kinase" The Journal of Biological Chemistry (Apr. 5, 1996), vol. 271, No. 14, pp. 8488–8492.

Varlamov, O. et al. "Induced and spontaneous mutations at Ser202 of carboxypeptidase E" The Journal of Biological Chemistry (Jun. 14, 1996), vol. 271, No. 24, pp. 13981–13986.

Primary Examiner—Bradley Sisson
Assistant Examiner—Enrique D. Longton
Attorney, Agent, or Firm—Amster, Rothstein & Ebenstein

[57] ABSTRACT

The present invention provides a novel method for the rapid isolation and identification of large numbers of novel enzyme substrates. The novel method provided by the present invention identifies substrates in tissue and/or cell extracts of a non-human model characterized as having an inactive enzyme. Without active enzyme, the substrates of this enzyme accumulate in the non-human model. The tissue or cell extract containing the enzyme substrate is then fractionated by passing the extract through an affinity column. The affinity column comprises an enzyme having similar specificity to the inactive enzyme, bound to a solid support. The affinity resin binds the enzyme substrate so that the substrate may be isolated from other proteins in the extract. The substrate of the enzyme may then be further identified by purifying and sequencing. Also provided by the present invention are novel substrates, and analogs of the substrates identified by the method of the present invention. The novel substrates are then processed and used in the development of therapeutics, such as in gene therapy and vaccines. Also provided by the present invention are receptors that bind to the protein, polypeptide, and peptide substrates of the present invention, and variations of these substrates for use in the development of drugs.

10 Claims, 4 Drawing Sheets

METHOD OF IDENTIFICATION OF NOVEL SUBSTRATES

STATEMENT OF GOVERNMENT INTEREST

This invention was made in part with government support under National Institutes of Health grant Nos. R01-DA-04494 and K02-DA-00194. As such, the government has certain rights in this invention.

BACKGROUND OF THE INVENTION

Peptide hormones and neurotransmitters are usually produced as larger pro-peptides, requiring a series of enzymes to generate the bioactive peptide (Docherty, K. and Steiner, D. F. (1982) *Ann. Rev. Physiol.*, 44, 625–638; Eipper, et al. (1986) Trends. Neurosci., 9, 463–468; Steiner, D. F. (1991). *In: Peptide Biosynthesis and Processing*, Fricker, L. D. (ed.), pp. 1–16, CRC Press, Boca Raton). Most of these cleavages occur at specific base residue sites, and enzymes that initially cleave the precursor have been identified (Smeekens, S. P. and Steiner, D. F. (1990) *J. Biol. Chem.* 265, 2997–3000; Seidah, et al. (1990) *DNA Cell. Biol.*, 9, 415–424; Hosaka, et al. (1991) *J. Biol. Chem.*, 266, 12127–12130; Kiefer, et al. (1991) *DNA Cell Biol.*, 10, 757–769; Nakagawa, et al. (1993) *J. Biochem.*, 113, 132–135). Following this initial cleavage, a carboxypeptidase is then usually required to remove the C-terminal basic residues from the peptide to produce the bioactive moiety (Fricker, L. D. (1988) *Ann. Rev. Physiol.*, 50, 309–321; Fricker, L. D. (1991). *In: Peptide Biosynthesis and Processing*, Fricker, L. D. (ed.), pp. 199–230, CRC Press, Boca Raton). For many years, a single carboxypeptidase was thought to be involved with the processing of most secreted peptides (Fricker, L. D. (1988) *Ann. Rev. Physiol.*, 50, 309–321; Fricker, L. D. (1991). *In: Peptide Biosynthesis and Processing*, Fricker, L. D. (ed.), pp. 199–230, CRC Press, Boca Raton). This enzyme is alternatively known as carboxypeptidase E (CPE), carboxypeptidase H, and ankephalin convertase, and has been designated EC 3.4.17.10 (Webb, E. C. (1986) *Eur. J. Biochem.*, 157, 1–26). CPE was initially discovered to be associated with the production of enkephalin in the adrenal medulla (Fricker, L. D. and Snyder, S. H. (1982) *Proc. Natl. Acad. Sci. USA* 79, 3886–3890), and has been found in all neuroendocrine tissues (Fricker, L. D. (1988) *Ann. Rev. Physiol.*, 50, 309–321; Fricker, L. D. (1991). *In: Peptide Biosynthesis and Processing*, Fricker, L. D. (ed.), pp. 199–230, CRC Press, Boca Raton; Schafer, et al. (1994) *J. Neurosci.*, 13, 1258–1279; Zheng, et al. (1994) *J. Neurosci.*, 14, 4656–4673). However, the view that CPE is the only intracellular peptide-processing carboxypeptidase has been challenged by the finding that mice with the fat mutation are still capable of producing insulin, albeit at lower levels. (Naggert, et al. (1995) *Nature Genetics*, 10, 135–142).

The fat mutation has been mapped to the CPE locus on Chromosome 8, and a point mutation has been found in the coding region (Naggert, et al. (1995) *Nature Genetics*, 10, 135–142). The point mutation converts $Ser^{202}$ into a Pro residue. When this mutation is created in the homologous rat CPE and the protein expressed in Sf9 cells using the Baculovirus system, the enzyme is inactive and is not secreted into the medium (Naggert, et al. (1995) *Nature Genetics*, 10, 135–142). Comparison of the enzyme activity measured between mutant and wild type CPE in the Baculovirus system showed that the mutation resulted in less than 0.1% activity of the wild type CPE. However, the levels of CPE-like-activity in $Cpe^{fat}/Cpe^{fat}$ mouse pituitary and pancreatic islets were found to be 5–10% of the levels in tissues from control mice (Naggert, et al. (1995) *Nature Genetics*, 10, 135–142). Furthermore, the C-terminal processing of insulin is not completely eliminated in the $Cpe^{fat}/Cpe^{fat}$ (Naggert, et al. (1995) *Nature Genetics*, 10, 135–142), suggesting that an active carboxypeptidase is present in the insulin secretory pathway of the $Cpe^{fat}/Cpe^{fat}$ mouse.

A newly reported enzyme, carboxypeptidase D (CPD), may be involved in the processing of secretory pathway peptides and partially compensate for the defective CPE in $Cpe^{fat}/Cpe^{fat}$ mice (Song, L. and Fricker, L. D. (1995) *J. Biol. Chem.*, 270, 25007–25013). CPD is present in bovine pituitary and adrenal (Song, L. and Fricker, L. D. (1995) *J. Biol. Chem.*, 270, 25007–25013) and in many rat tissues (L. Song and L. Fricker, unpublished). In contrast, CPE is present mainly in neuroendocrine tissues, and undetectable levels in liver (Zheng, et al. (1994) *J. Neurosci.*, 14, 4656–4673; Fricker, et al. (1989) *Mol. Endocrinol.*, 3, 666–673). The major difference between the two enzymes is the size; CPE is approximately 50–56 kDa, whereas CPD is 180 kDa in bovine pituitary (Song, L. and Fricker, L. D. (1995) *J. Biol. Chem.*, 270, 25007–25013) and 100–180 kDa in various rat tissues (L. Song and L. Fricker, in preparation). CPD is not recognized by antisera raised against the N- or C-terminal regions of CPE (Song, L. and Fricker, L. D. (1995) *J. Biol. Chem.*, 270, 25007–25013).

It has recently been found that a mutation responsible for obesity in the $Cpe^{fat}/Cpe^{fat}$ mouse maps to the CPE gene locus, and that a point mutation is found within the $Cpe^{fat}/Cpe^{fat}$ mouse gene (Naggart, et al. *Nature Genetics* 10, 135 (1995)). This point mutation causes CPE to be inactive, and degrades within the cell (Varlamov, et al. *J. Biol. Chem.*, 271, 13981 (1996)). As stated above, the absence of CPE leads to defects in the processing of insulin (Naggart, et al. *Nature Genetics* 10, 135 (1995)). In the brain, a defect was found in the processing of enkephalin (Fricker, et al. *J. Biol. Chem.*, 271:30614–30624 (1996)), and another group found a defect in the processing of neurotensin and melanin-concentrating hormone (Rovere, et al., *Endocrinology*, 137, 2954 (1996)). In all cases, the amount of the correctly processed peptide is decreased in the $Cpe^{fat}/Cpe^{fat}$ mouse. Whereas in normal mouse tissues there are virtually no peptide intermediates containing C-terminal basic residues, these intermediates accumulate to high levels in the $Cpe^{fat}/Cpe^{fat}$ mouse.

It is likely that the obesity-causing defect in the $Cpe^{fat}/Cpe^{fat}$ mouse is due to a novel peptide because the physiological changes of these mice do not resemble those produced by the known peptides. The $Cpe^{fat}/Cpe^{fat}$ mouse is not extremely hyperphagic, and regulate body weight more through metabolic changes than through increased feeding. Peptides such as neuropeptide Y are not likely candidates because they stimulate feeding, and the absence of these peptides would be expected to produce skinny mice. Although there are peptides known to inhibit feeding, the primary change in the $Cpe^{fat}/Cpe^{fat}$ mouse is metabolic, and is not likely to be mediated by the known peptides. Accordingly, a method for the identification of peptides that are not correctly processed in the $Cpe^{fat}/Cpe^{fat}$ mouse would be extremely useful, as peptides identified by this method have the potential to be used in therapeutics to control obesity.

Cells communicate with each other using a variety of signaling molecules. Many of these signaling molecules are peptides that are secreted from one cell type, and then bind to a receptor on a second cell type. A large number of therapeutics are based on peptides. In some cases, the peptide itself is the therapeutic (for example, insulin). In other cases, the actual therapeutic is a compound which mimics the action of the peptide by binding to the peptide's receptor and either stimulating or blocking the receptor action (for example, morphine, which binds to the receptors for enkephalin and other endogenous opiate peptides).

Current approaches for identifying individual substrates for enzymes and receptors are extremely time consuming. Over the past 50 years a number of peptides have been discovered largely by chance, and not through a systematic search based on the relative abundance of each peptide in the brain or other tissues. For example, the enkephalins were discovered by their ability to mimic the action of an opiate drug in a bioassay. If plants did not produce opiates, then it is unlikely that the enkephalin would have been discovered. It is widely estimated that only half of all peptides have been discovered. A rapid method of identifying peptides and other molecules that interact with enzymes and receptors is greatly needed for identifying all enzyme and receptor substrates. For example, many G-protein-coupled receptors bind peptides, and it is likely that a large number of these orphan receptors have undiscovered peptide ligands. Specifically, polypeptide hormones, after binding to their membrane-located receptors, induce changes in the membrane-bound G proteins, which are currently little understood. A rapid method of identifying the polypeptide hormones that bind to the membrane-located receptors would aid tremendously in understanding membrane-bound G-proteins. A rapid method of identification of enzyme substrates would decrease the time required for identifying possible drugs, and would accordingly decrease the overall time and expenses required for the process of the research, design and development of drugs.

SUMMARY OF THE INVENTION

The existing need for a rapid method of identifying novel enzyme substrates is met by the method provided by the present invention. The method provided by the present invention sets forth a novel combination of methods and principles which allows for the rapid and accurate isolation and identification of a large number of enzyme substrates. The novel method provided by the present invention identifies substrates in tissue and/or cell extracts of a non-human model characterized as having an inactive enzyme. Without active enzyme, the substrates of this enzyme accumulate in the non-human model. The tissue or cell extract containing the substrate is then fractionated by passing the extract through an affinity column. The affinity column comprises an enzyme having similar specificity to the inactive enzyme, bound to a solid support, such as a resin. The affinity resin binds the substrate so that the substrate may be isolated from other proteins in the extract. The substrate of the enzyme may then be further identified by purifying and sequencing. The present invention also provides for novel substrates identified using the method of the present invention. After isolation, the novel substrates are processed and used in a wide range of therapeutics and diagnostics. For example, the novel processed substrates may be used to identify receptors, and novel variations of the substrates may be useful as agonists, antagonists, partial agonists, and partial antagonists. Also provided are novel single-stranded nucleic acid probes and novel antibodies for detection of the novel substrates. Further provided is a recombinant vector encoding a novel substrate for use in gene therapy to treat a disease associated with a defective enzyme. The novel processed substrates identified by the method of the present invention may be used directly in the development of therapeutics and diagnostics in a wide range of areas, including gene transfer, vaccines, and detection and/or diagnosis of a disease or condition associated with a defective enzyme.

In a preferred embodiment of the invention, tissue extracts are obtained from a $Cpe^{fat}/Cpe^{fat}$ mouse, which has a mutation in the CPE enzyme. This embodiment identifies bioactive peptides in these tissues by identifying those peptides having a C-terminal basic residue, thereby identifying peptides which are substrates for carboxypeptidase E and thus likely to be bioactive peptides. The carboxypeptidase E of a $Cpe^{fat}/Cpe^{fat}$ mouse is inactive, based upon the information that the mutation responsible for obesity in the $Cpe^{fat}/Cpe^{fat}$ mouse maps to the carboxypeptidase E locus. Therefore, in this embodiment, all peptides having C-terminal basic residues that are identified in the $Cpe^{fat}/Cpe^{fat}$ mouse are peptides that are not correctly processed and are thus presumably substrates for CPE, and likely to be bioactive peptides. Because it is believed that the $Cpe^{fat}/Cpe^{fat}$ mouse is obese because of a peptide which has not been correctly processed and is inactive, the identification of these peptides could lead to the development of a large number of therapeutics to control obesity.

Additional objects of the invention will be apparent from the description which follows.

BRIEF DESCRIPTION OF THE FIGURES

FIG. 1: FIG. 1 sets forth the binding of wild type CPE (wt), $K^{342}CPE$ (K), and $Q^{342}CPE$ (Q) to p-aminobenzoyl-Arg Sepharose. Wt CPE and the two mutants were expressed in the baculovirus system. Left: Media from the baculovirus expression was analyzed on a Western blot, using antiserum directed against CPE to detect this protein. Middle: The media was applied to a 0.5 ml column of p-aminobenzoyl-Arg Sepharose and the unbound material analyzed on a Western blot for CPE immunoreactivity. Right: Bound CPE was eluted from the resin with 25 mM Arg, and the amount of CPE determined by Western blot analysis.

FIG. 2: FIG. 2 sets forth the LC/MS of affinity purified material from control (top) and $Cpe^{fat}/Cpe^{fat}$ (bottom) mouse brains. Peptides purified from 2 brains were analyzed by liquid chromatography/electrospray mass spectrometry (LC/MS), using a reverse phase C18 HPLC column in 0.1% trifluoroacetic acid and an increasing gradient of acetonitrile to elute the peptides. Approximately 5% of the liquid chromatography output was sent directly to the electrospray mass spectrometer, and the remainder was collected into tubes. The mass spectrometer scanned the samples 13 times per minute. The total ions with a m/z>300 Da in the 26 scans collected over the period from 32 to 34 minutes are shown, after subtraction of background at 30 and 36 minutes.

FIG. 3.

FIG. 4.

DETAILED DESCRIPTION OF THE INVENTION

The novel method of the present invention allows for the rapid isolation and identification of large numbers of substrates. The substrates identified may be, for example, molecules that bind to enzymes or receptors. The novel method of the present invention identifies substrates in tissue and/or cell extracts of a non-human model characterized as having an inactive enzyme. Without an active enzyme, the substrates of this enzyme accumulate in the non-human model. A tissue or cell extract which contains substrates to be identified is then fractionated by passing the extract through an affinity column. The affinity column comprises an enzyme or protein having similar binding specificity as the inactive enzyme, bound to a solid support, such as a resin. The affinity resin binds the substrate so that the substrate may be isolated from other proteins in the extract. Where multiple substrates are present, the substrates are further fractionated. The substrates may then be further identified using standard purification and sequencing techniques.

As used herein, an "enzyme" is a protein that functions as a catalyst in a particular reaction. An enzyme "substrate" is a molecule that binds to the enzyme, for which the enzyme has specificity. An "enzyme-substrate complex" is herein defined as the enzyme bound to a substrate, and includes an enzyme bound to more than one substrate at any given time.

The method of the present invention may be used to identify novel substrates of a wide variety of enzymes. Specific non-limiting examples of enzymes for which their substrates may be identified using this method are peptidases, reductases, kinases, ligases, convertases, synthetases, hydrolases, phosphatases, amidation enzymes and polymerases. Further non-limiting examples of peptidases which may be employed in the method of the present invention for the identification of novel substrates include, but are not limited to, carboxypeptidase E, carboxypeptidase A, carboxypeptidase B, carboxypeptidase D, carboxypeptidase M, carboxypeptidase N, carboxypeptidase U, and carboxypeptidase Z. In a preferred embodiment of the invention, the novel substrates of interest are those which bind to carboxypeptidase E.

Specifically, the present invention provides for a method of identifying a novel enzyme substrate of a non-human model wherein the non-human model has an inactive enzyme. Examples of non-human models that may be employed in the method of the present invention include eukaryotes and prokaryotes. Non-limiting examples of eukaryotes are mice, rabbits, rats, hamsters, pigs, fish, ducks, and drosophila, and non-limiting examples of prokaryotes are viruses and bacteria.

The inactive enzyme of the non-human model may be generated by a knockout mutation. As used herein, a "knockout" mutation is a mutation in a gene which encodes a protein which renders the protein inactive. Knockout mutations may be generated by homologous targeting of the gene, as done for the enzymes furin and prohormone convertase 2, and may be generated in mice, drosophila, and bacteria. These organisms may be used in the investigation of apoptosis, neoplasia, cell proliferation, signal transduction, and drug screening. It is to be understood that the application of the method of the present invention is not limited to particular non-human models or to particular mutations in the non-human models.

It is to be understood that any one of a number of tissues or cells of the non-human model can be employed by the methods of the present invention for the identification of novel substrates. Examples include, but are not limited to, brain, heart, duodenum, testis, ovary, skeletal muscle, lung, liver, kidney, spleen, thymus, stomach, veins, arteries, glands, colon, pancreas, and intestine. In a preferred embodiment of the invention, brain tissue is obtained from the $Cpe^{fat}/Cpe^{fat}$ mouse and used in the method of the present invention.

Tissue or cell-containing extracts are obtained from the non-human model and are fractionated on an affinity resin column. The affinity resin of the column comprises an enzyme or protein bound to a solid support, the enzyme or protein having similar specificity to said inactive enzyme of the non-human model. The affinity resin binds the substrate to the column. Examples of types of affinity resin columns are known to those skilled in the art, and include, but are not limited to, gel affinity columns, DEAE Sephacel affinity columns, and phosphocellulose affinity columns. In a preferred embodiment of the invention, the affinity resin of the column comprises a CPE enzyme bound to a solid support. The CPE enzyme bound to the solid support is inactive and has retained its ability to bind to a substrate. In order to achieve this, CPE is mutated so that it remains inactive, but still can bind to substrates. In a preferred embodiment of the invention, the affinity column comprises a mutated CPE bound to a solid support wherein the mutation is created by conversion of $Glu^{342}$ to $Gln^{342}$. In addition, CPE can also be bound to a solid support in the presence of a thiol-directed inhibitor such as mercuric chloride ($HgCl_2$) or p-chloromercuriphenyl sulfonate. These inhibitors prevent CPE from cleaving substrates, but do not interfere with the binding of the substrates. The chelation of the active site metal from CPE may also inactivate the enzyme without affecting the ability of the enzyme to bind substrates; this approach has previously been used with carboxypeptidase B (Yasuhara and Ohasi (1990) *Biochem. Biophys. Res. Comm.* 166:330–335). Another approach is to chemically modify an enzyme so that it binds, but does not cleave CPE substrates. An example of this is anhydrotrypsin, which binds peptides with C-terminal basic residues but is enzymatically inactive. Anhydrotrypsin agarose is functionally similar to the CPE affinity columns, and all of these resins are able to isolate CPE substrates. In a preferred embodiment of the invention, the resin comprising a mutated CPE bound to a solid support specifically isolates substrates present in the $Cpe^{fat}/Cpe^{fat}$ mouse brain that have C-terminal basic residues, such as arginine and lysine. All peptides having C-terminal basic residues that are identified and elevated in the $Cpe^{fat}/Cpe^{fat}$ mouse are presumably substrates for CPE, and are thus likely to be bioactive peptides.

The elute fractions containing the substrate from the affinity column are collected and the substrate is purified and sequenced for further identification. Examples of isolation and purification methods include, but are not limited to, high performance liquid chromatography (HPLC) with reverse phase columns, ion exchange columns, and gel filtration columns. In a preferred embodiment of the invention, the substrates are purified from the elute fractions by HPLC.

The method of the present invention further comprises sequencing of the substrates obtained from the elute fractions of the affinity column. Methods by which the substrates identified by the method of the present invention may be sequenced are known to those skilled in the art and include methods such as the Edman degradation procedure and various mass spectrophotometer procedures. In order to generate substantial amounts of the substrate for peptide sequencing, the purification steps of the method of the present invention may be scaled up by methods known to those skilled in the art.

The present invention also provides for novel substrates which have been identified by the method of the present invention. As used herein, a novel "substrate" may be a protein, polypeptide, peptide, RNA, antisense RNA, double-stranded RNA, DNA-RNA hybrid, double-stranded DNA, nucleotides, oligonucleotide or antisense oligonucleotide, and include both processed and unprocessed substrates. The proteins may be, for example, ribosomal, lysosomal, membrane, transmembrane, oncoproteins, histone, regulatory, neurotransmitter, G proteins, hormonal, nuclear, ribonuclear, and signal sequencing proteins, and may be phosphorylated or dephosphorylated. The novel RNA substrates of the present invention may be, for example, mRNA, rRNA, tRNA and other small RNAs.

The present invention also provides for novel substrates, such as proteins and peptides, that bind to receptors, (i.e., proteins or peptides that are ligands) either directly or after enzymatic processing by the active form of the enzyme. As used herein, a "ligand" is a molecule that binds to a receptor to alter its function. A "substrate" is the material that accumulates in the non-human model with a defective enzyme, and a "reaction product" is the material produced from the substrate by the active form of the enzyme. The substrate itself may not be a ligand for the receptor, but may require activation by the enzyme to form the reaction product. In a preferred embodiment of the invention, the method presented by the present invention employs the $Cpe^{fat}/Cpe^{fat}$ mouse, and the isolated substrates require processing by the active form of carboxypeptidase E to remove C-terminal basic amino acids and generate the form of the peptide that binds to a receptor. The novel substrates may be agonists, antagonists, partial agonists, or partial antagonists, and are identified as such using receptor binding competition assays together with bioassays, using techniques which are commonly known to those skilled in the art. In a preferred embodiment of the invention, the novel substrates are converted to the normal physiological products by reaction with active carboxypeptidase E, and these reaction products function as ligands which bind to neurotransmitter receptors, hormone receptors, and growth factor receptors.

Also encompassed by the present invention are nucleotide or oligonucleotide sequences that encode novel substrates that inhibit or alter the activity of a gene by directly binding to the nucleotide sequence of a gene and modulating its activity. Further included are nucleotide or oligonucleotide sequences that encode novel processed substrates that functionally replace a gene. The functional replacement of a gene may be accomplished, for example, through homologous recombination and by other methods known to one skilled in the art.

Also intended to be encompassed by this invention are analogs of the novel processed and unprocessed substrates of the present invention. As used herein, "analog" means a functional variant of the substrate. The analogs of the substrates may vary by one or more amino acids or nucleic acids, while maintaining or enhancing the affinity and/or specificity of the analog.

Once a novel substrate has been identified, purified, and sequenced, the corresponding human substrate may then be identified. In the instance where the novel substrate is a protein, polypeptide, or peptide, the nucleic acid sequence that encodes the novel protein, polypeptide, or peptide must first be determined. This may be done by deducing the nucleic acid sequence from the amino acid sequence, preparing an oligonucleotide, and screening a human cDNA library. If the conservation of the sequence is not sufficient between the organism used to isolate the initial substrate and human to permit cloning of the human cDNA using oligonucleotide probes, the oligonucleotide probe may first be used to isolate a cDNA from the organism used to isolate the initial substrate, and then this cDNA may be used to screen human cDNA libraries. The oligonucleotide probes may be obtained from a commercial source (Genset, Genelink, Perkin-Elmer, or other sources), and may be labeled with $^{32}P$ using methods commonly known to those skilled in the art. The cDNA libraries may be obtained from a commercial source (Clontech) and are plated onto an appropriate membrane (nitrocellulose or Nytran, Scheicher and Schuell; Genescreen, DuPont/NEN). The membrane will be allowed to hybridize with the labeled oligonucleotide probe, the unbound probe is removed by washing, and then the cDNA hybridizing with the oligonucleotide is detected using an appropriate method, many of which are known to one skilled in the art. The bacterial colony or bacteriophage plaque corresponding to the cDNA on the membrane will be recovered, amplified, and rescreened as described above, until a single colony or plaque that hybridizes to the oligonucleotide is obtained. This clone may be sequenced using the standard dideoxynucleotide method, also known to those skilled in the art. The amino acid sequence is then deduced from the nucleotide sequence, based on the genetic code.

The deduced amino acid sequence of the precursor of the substrate is used to learn the sequence of the human peptide, and to predict additional bioactive peptides. Pairs of basic amino acids, most commonly Lys-Arg and Arg-Arg, typically denote the cleavage sites found in the precursors of bioactive peptides. In some instances, the pairs of basic amino acids are separated by 2, 4, or 6 residues, and the resulting consensus site for endopeptidase cleavage is Arg-X-X-Arg, Arg-X-X-X-X-Arg, or Arg-X-X-X-X-X-X-Arg with the cleavage occurring after the second basic residue. Additional requirements for cleavage sites are known (Devi, L. (1991) *In: Peptide Biosynthesis and Processing*. Fricker, L. D. (ed.), pp. 175–198, CRC Press, Boca Raton). Following endopeptidase cleavage at the basic amino acid sites, a carboxypeptidase then removes the C-terminal basic residues (Fricker, L. D. (1991) *In: Peptide Biosynthesis and Processing*. Fricker, L. D. (ed.), pp. 199–230, CRC Press, Boca Raton). If a Gly is then present on the C-terminus after the basic residues have been removed, this Gly is converted into a C-terminal amide residue (Bradbury, A. and Smyth, D. (1991) *In: Peptide Biosynthesis and Processing*. Fricker, L. D. (ed.), pp. 232–250, CRC Press, Boca Raton). Therefore, the bioactive peptides predicted from the precursor would start immediately after (i.e. C-terminal side of) a basic amino acid cleavage site and would continue to the last residue before (i.e. N-terminal side of) the next basic amino acid cleavage site until this last residue were a Gly, at which point the peptide would end one residue earlier and have a C-terminal amide group. For a typical peptide precursor, the predicted bioactive peptide would be the sequences between Lys-Arg and/or Arg-Arg sites.

The novel substrate obtained by the method of the present invention and the corresponding human substrate, once identified, may be obtained using methods commonly known to those skilled in the art. For example, the novel substrate may be isolated from fractions obtained from an affinity column, it may be isolated from native cells, or it may be recombinantly produced. In addition, mutated nucleic acid sequences that encode novel substrates can be prepared using site mutagenesis techniques. The protein, polypeptide and peptide substrates may also be synthesized by methods commonly known to one skilled in the art (*Modern Techniques of Peptide and Amino Acid Analysis*, John Wiley & Sons (1981); M. Bodansky, *Principles of Peptide Synthesis*, Springer Verlag (1984)). Examples of methods that may be employed in the synthesis of the substrates and analogs of the present invention include, but are not limited to, solid phase peptide synthesis, solution method peptide synthesis, and synthesis using any of the commercially available peptide synthesizers. The protein, polypeptide and peptide substrates, and analogs thereof, may contain coupling agents and protecting groups used in the synthesis of the substrates, and are well known to one of skill in the art. Examples of coupling agents include, but are not limited to, 1-ethyl-3-(3-dimethylaminopropylcarbodiimide (DCC) and diisopropyl carbodimide (DIPI). Examples of protecting groups include, but are not limited to, PyBrOP, BOC, tBu, Fmoc, z, OBzl, OtBu, Bz, OMe, and $NH_2$ (Greene, T. *Protective Groups in Organic Synthesis*, Academic Press (1981)).

The present invention also provides novel single-stranded nucleic acid probes for use in diagnosing and detecting a disease or disorder caused by a defective enzyme. The nucleic acid probes may be DNA, cDNA, or RNA, and are prepared from the nucleic acid sequences encoding the novel substrates, or the corresponding human nucleic acid sequence. The probes may be the full length sequence of the nucleic acid sequence encoding the novel substrate, or fragments thereof. Typical probes are 12 to 40 nucleotides in length. Generally, the probes are complementary to the nucleic acid sequence that encodes the novel substrate, although probes to introns are also contemplated. The probes may be synthesized using an oligonucleotide synthesizer, and may be labeled with a detectable marker such as a fluorescence, enzyme or radiolabeled markers including $^{32}P$ and biotin, and the like. Combinations of two or more labeled probes corresponding to different regions of the nucleic acid sequence encoding the novel substrate also may be included in kits to allow for the detection and/or analysis of the nucleic acid sequence by hybridization.

Specifically, the novel nucleic acid sequences may be used to produce probes capable of identifying the nucleic acids which encode a novel substrate, which probes can be used in the identification, treatment and prevention of diseases associated with a defect in an enzyme, to assess the susceptibility of a subject to a defective enzyme, and to determine whether various drugs are effective to treat the condition caused by the defective enzyme. The antibodies may be labeled with standard detectable markers (e.g. chemiluminescent detection systems and radioactive labels such as $^{125}I$) for detecting novel substrates. The antibodies may also be presented in kits with detectable labels and other reagents and buffers for such detection.

The presence of the novel substrate in a sample may be determined by detecting the nucleic acid encoding the novel substrate or the expression products of the nucleic acid sequence. Such expression products include both mRNA as well as the novel substrate itself. mRNA expression may be detected by standard sequencing techniques, hybridization with one or more probes hybridizable to the novel substrate mRNA using standard procedures such as Northern blot analysis, dot and slot hybridization, S1 nuclease assay, or ribonuclease protection assays, polymerase chain reaction using sense and antisense primers prepared from the nucleic acid sequences encoding the novel substrate, and combinations thereof. The presence of the novel substrate in a sample may be detected using antibodies to the novel substrate by procedures known in the art including, but not limited to, immunoblotting, immunoprecipitation, solid phase radioimmunoassay (e.g. competition RIAs, immobilized antigen or antibody RIAs, or double antibody RIAs), enzyme-linked immunoabsorbant assay, and the like.

The present invention also provides an antibody immunoreactive with a novel processed substrate, or an analog of a novel substrate, isolated by the method of the present invention. The antibodies may be monoclonal or polyclonal and are produced by standard techniques known to one skilled in the art.

The present invention additionally provides the use of a nucleic acid sequence which encodes a novel substrate of the present invention in gene therapy for treatment and/or prevention of a disease. The nucleic acid sequence encoding the novel substrate of the present invention may be introduced into the cells of a subject by a number of procedures known to one skilled in the art, such as electroporation, DEAE Dextran, monocationic liposome fusion, polycationic liposome fusion, protoplast fusion, DNA coated microprojectile bombardment, by creation of an in vivo electrical field, injection with recombinant replication-defective retroviruses, homologous recombination, and naked DNA transfer. It will be appreciated by those skilled in the art that any of the above methods of DNA transfer may be combined.

The present invention also provides a recombinant viral vector comprising (a) the nucleic acid of or corresponding to at least a portion of the genome of a virus, which portion is capable of directing the expression of a novel nucleic acid sequence encoding a novel substrate, or analog thereof, and (b) the novel nucleic acid sequence encoding the novel substrate, or analog thereof, identified by the method of the present invention operably linked to the viral nucleic acid and capable of being expressed as a functional gene product in the target cell. The recombinant viral vectors of the present invention may be delivered from a variety of viral nucleic acids known to one skilled in the art, e.g. the genomes of HSV, adenovirus, adeno-associated virus, Semiliki Forest virus, vaccinia virus, and other retroviruses or DNA viruses.

The recombinant vectors of the present invention also contain a nucleotide sequence encoding suitable regulatory elements so as to effect expression of the vector construct in a suitable host cell. As used herein, "expression" refers to the ability of the vector to transcribe the inserted DNA sequence into mRNA so that synthesis of the protein encoded by the inserted nucleic acid can occur. Those skilled in the art will appreciate that a variety of enhancers and promoters are suitable for use in the constructs of the invention, and that the constructs will contain the necessary start, termination, and control sequences for proper transcription and processing of the DNA sequence encoding a protein when the recombinant vector construct is introduced into a host cell.

Vectors suitable for the expression of the DNA sequence encoding a novel substrate in a cell are well known to those skilled in the art and include pET-3d (Novagen), pProEx-1 (Life Technologies), pFastBac 1 (Life Technologies), pSFV (Life Technologies), pcDNA II (Invitrogen), pSL301 (Invitrogen), pSE280 (Invitrogen), pSE380 (Invitrogen), pSE420 (Invitrogen), pTrcHis A,B,C (Invitrogen), pRSET A,B,C (Invitrogen), pYES2 (Invitrogen), pAC360 (Invitrogen), pVL1392 and pV11392 (Invitrogen), pCDM8 (Invitrogen), pcDNA I (Invitrogen), pcDNA I(amp) (Invitrogen), pZeoSV (Invitrogen), pcDNA 3 (Invitrogen), pRc/CMV (Invitrogen), pRc/RSV (Invitrogen), pREP4 (Invitrogen), pREP7 (Invitrogen), pREP8 (Invitrogen), pREP9 (Invitrogen), pREP10 (Invitrogen), pCEP4 (Invitrogen), pEBVHis (Invitrogen), and λPop6. Other vectors would be apparent to one skilled in the art.

Suitable promoters include, but are not limited to, constitutive promoters, tissue specific promoters, and inducible promoters. Some eukaryotic vectors have been engineered so that they are capable of expressing inserted nucleic acids to high levels within the host cell. Such vectors utilize one of a number of powerful promoters to direct the high level of expression. Eukaryotic vectors use promoter-enhancer sequences of viral genes, especially those of tumor viruses.

The present invention also provides a method for treating a disease or disorder in a subject in need of such treatment comprising the delivery and expression of a novel substrate of the present invention into a sufficient number of cells of the subject, preferably bone marrow cells, to treat the subject. The novel substrate of the present invention may be delivered into the subject's cells by a number of procedures known to one skilled in the art, including, for example, electroporation, DEAE dextran, cationic liposome fusion, protoplast fusion, DNA coated microprojectile bombardment, injection with recombinant-defective retroviruses, homologous recombination, and the like. Accordingly, a stem cell which expresses the novel substrate of the present invention introduced therein through viral transduction, homologous recombination, or transfection is also provided by the present invention.

For the purposes of naked DNA transfer into cells, a recombinant vector contains the nucleic acid encoding a novel substrate of the present invention may be combined with a sterile aqueous solution which is preferably isotonic with the blood of the recipient. Such formulations may be prepared by suspending the recombinant vector in water containing physiologically compatible substances such as sodium chloride, glycine, and the like, and having buffered pH compatible with physiological conditions to produce an aqueous solution, and rendering such solution sterile.

The present invention also provides a method of treating mammals afflicted with a condition associated with a defective enzyme which comprises the step of administering to the individual a therapeutically effective amount of a novel substrate of the present invention in a pharmaceutically acceptable composition. Administration of the composition may be for either a prophylactic or therapeutic use. When provided prophylactically, the composition is provided in advance to the symptom caused by the condition afflicting the individual. When provided therapeutically, the composition is provided at, or shortly after, the onset of any symptoms of the disease. The therapeutic administration of the composition serves to attenuate the condition. Examples of conditions and diseases which can be treated using a composition containing a novel processed substrate or substrates of the present invention include obesity, neurological diseases, and growth hormone dysfunctions. Veterinary uses are also intended to be encompassed by this invention.

The amount of the composition containing the novel substrate(s) administered will vary upon the stage of progression of the disease or syndrome, the weight of the individual, and the efficacy of the composition containing the novel substrate(s). One of skill in the art will know the parameters to evaluate the response of the individual to the composition containing the novel substrate(s) and establish the dosage based on those parameters. Such therapies may be administered as often as necessary and for the period of time judged necessary by the treating physician.

Further provided by the present invention is the use of the novel substrates of the present invention as vaccines. These vaccines can be used to treat and prevent a wide variety of diseases. To form a vaccine, the recombinant vector of the present invention is administered in conjunction with a suitable pharmaceutical carrier. Representative examples of suitable carriers include, but are not limited to, mineral oil, alum, and synthetic polymers. Vehicles for vaccines are well known in the art and the selection of a suitable vehicle is deemed to be within the scope of those skilled in the art from the teachings contained herein. The selection of a suitable vehicle is also dependent on the manner in which the vaccine is to be administered. The vaccine may be in the form of an injectable dose, and may be administered intramuscularly, intravenously, orally, intradermally, intranasally, or subcutaneously.

In the preferred embodiment of the invention, novel substrates that are associated with obesity are identified using the method of the present invention. It is believed that the $Cpe^{fat}/Cpe^{fat}$ mouse is obese because of a peptide which has not been correctly processed and is inactive, thus the peptides identified and processed by the methods of the present invention may be used in the development of a large number of therapeutics to control obesity.

The present invention is described in the following Experimental Details Sections which is set forth to aid in the understanding of the invention, and should not be construed to limit in any way the invention as defined in the claims which follow thereafter.

EXPERIENTIAL DETAILS SECTION

A. Materials and Methods

Animals

Mutations of CPE

To create point mutations within CPE, the cDNA encoding full length rat CPE protein was subcloned into the pALTER vector (Promega). $Glu^{342}$ ($E^{342}$), numbering from the first Met of preproCPE, was converted to either a Lys (K) or Gln (Q) using the appropriate oligonucleotide to change the codon. The standard method recommended by Promega was used for this procedure. The nucleotide sequence of the product was confirmed by double stranded DNA sequencing.

Expression and Characterization of CPE and CPE Mutants

The cDNA encoding CPE or one of the CPE mutants was subcloned into the pVL1393 baculovirus expression vector, and recombinant virus was generated using the Baculogold method (Invitrogen). The standard method recommended by Invitrogen was used for this procedure. Large scale cultures (typically 1 liter) of Sf9 cells were infected with recombinant virus expressing CPE or one of the mutants. Three days after infection, the CPE was recovered from the media by purification on p-aminobenzoyl-Arg Sepharose, as described (Fricker, et al. (1990) *J. Biol. Chem.* 65, 2476–2482). Enzyme activity was measured using the substrate dansyl-Phe-Ala-Arg, as described (Fricker (1995) *Method of Neuroscience*, 23, 237–250).

Creation of Immobilized CPE Affinity Column

Purified wild type CPE or $Q^{342}CPE$ (0.2 to 2 mg were combined with 0.4 ml of Affigel-15 (BioRad) in 50 mM sodium phosphate pH 8.0 buffer and shaken for 75 minutes at room temperature. Then, 50 $\mu$l of 1 M ethanolamine hydrochloride (pH 8) were added and the mixture shaken for another 45 minutes. The Affigel resin was then poured into a plastic column. The resin was washed first with 10 ml of 50 mM sodium phosphate pH 8.0, then with 10 ml of 100 mM sodium acetate pH 5.5 containing 1 M NaCl and 1% Triton X-100, and then with 10 ml of 100 mM sodium acetate pH 5.5 containing 0.01% Triton X-100.

Characterization of Affinity Columns

To demonstrate that the immobilized CPE resin could extract a CPE substrate from a solution, without cleaving the substrate, 100 nmoles of dansyl-Phe-Ala-Arg were incubated with immobilized CPE in 3 ml of 0.1 M NaAc pH 5.5 buffer containing 1 M NaCl and 1% Triton X-100 for 16 hrs at 4° C. Then, the unbound material was recovered by filtration, and the resin was washed with 3 ml of the same buffer. The amount of peptide in the combined eluate and wash fractions was determined by measuring fluorescence (excitation 350 nm, emission 500 nm). The amount of peptide extracted by the resin was calculated as the difference between the amount applied (100 nmoles) and the amount recovered in the eluate/wash fraction. The % of peptide converted to dansyl-Phe-Ala was determined by extracting the material with chloroform and measuring the fluorescence of this organic phase.

To demonstrate that the immobilized CPE resin could be used to purify a CPE substrate from a solution, 5 nmoles of dansyl-Phe-Ala-Arg were applied to a 0.4 ml column containing the immobilized Q342 CPE (0.1 mg on Affigel 15, in 0.1 M NaAc pH 5.5 buffer containing 0.01% Triton X-100 and 1 mM $HgCl_2$. The column flow through was re-applied to the column twice, and then the column was washed with 3 ml 0.1 M NaAc pH 5.5 containing 1 M NaCl and 1% Triton X-100 The column was rinsed with 3 ml of 10 mM NaAc, pH 5.5, and eluted with 3 ml of 20 mM Tris pH 8.0 containing 0.01% Triton X-100 and 25 mM Arg. The amount of peptide in each fraction was determined by measuring the fluorescence (excitation 338 nm, emission 558 nm).

To demonstrate that immobilized anhydrotrypsin resin could also bind a CPE substrate, 100 nmoles of dansyl-Phe-Ala-Arg were applied to 0.3 ml of anhydrotrypsin agarose (Takara Biomedicals) in 2 ml of 50 mM NaAc buffer, pH 5.0, containing 500 mM NaCl, 0.5% 3[(3-cholamidopropyl)-dimethylammonio]-1-propane sulfonate (CHAPS), and 20 mM $CaCl_2$. The resin was washed first with 8 ml of the same buffer, and then with 12 ml of 10 mM NaAc pH 5.0 containing 20 mM $CaCl_2$. The bound peptide was eluted with 2 ml of 5 mM HCl. The amount of peptide in each fraction was determined by measuring the fluorescence (excitation 350 nm, emission 570 nm); for the elute samples, 100 µl 1 M NaAc, pH 5.0 and 50 µl 10% CHAPS were added to improve the fluorescence of the peptide.

Extraction and Affinity Column Purification of Peptides from Control and Fat/fat Mouse Brain Brains from $Cpe^{fat}/Cpe^{fat}$ mice (3) or control littermates (3) were removed from the animals and stored frozen at −80° C. until analysis. To extract the peptides, the frozen brains were placed into 5 ml of boiling 0.1 M acetic acid and homogenized using a Brinkmann Polytron. The mixture was incubated in a boiling water bath for 30 minutes, cooled to room temperature, and centrifuged for 30 minutes at 50,000 g. The supernatant was filtered through a Centricon 10 microfiltration device (Arnincon). The filtrate was neutralized to pH 5.0 with 0.5 ml of 1 M NaOH and 1 ml of 1 M NaAc, pH 5.0. CHAPS and $CaCl_2$ were added to 0.5% and 20 mM final concentrations, respectively. An aliquot was saved for radioimmunoassay, and the remainder was applied to 0.3 ml of anhydrotrypsin agarose. The resin was washed with 25 ml of 50 mM NaAc, pH 5.0 containing 0.5% CHAPS, 20 mM $CaCl_2$, and 500 mM NaCl, and then with 25 ml 10 mM NaAc pH 5.0 containing 20 mM $CaCl_2$. Bound peptides were eluted with 2 ml of 5 mM HCl. Aliquots of each fraction were used for radioimmunoassay.

Radioimmunoassay of Endogenous Peptides in Brain Extracts

To determine the efficiency of the affinity column, a radioimmunoassay (RIA) was performed to measure Leu.enkephalin (Enk). The RIA for Enk was performed using an RIA kit (Peninsula Laboratories). This assay is specific for Enk, and does not recognize C-terminally extended peptides. To measure the amount of Enk-$Arg^6$ and/or Enk-$Arg^6$-$Arg^6$, an aliquot of each fraction was treated with 0.5 ng of carboxypeptidase B (Sigma) for 2 hours at 37° C. in 100 mM Tris Cl buffer, pH 8.5, containing 0.1% Triton X-100. Carboxypeptidase B removes C-terminal basic residues and converts the Enk-$Arg^6$ and/or Enk-$Arg^6$-$Arg^7$ into Enk which is subsequently detected by the RIA. The reaction was terminated by boiling for 5 minutes. The amount of Enk in each sample, with or without carboxypeptidase B treatment, was determined using the RIA kit, as recommended by the manufacturer.

Liquid Chromatography/mass Spectrometry of Affinity-purified Peptides

Peptides purified from brain extracts of $Cpe^{fat}/Cpe^{fat}$ mice were analyzed by liquid chromatography/electrospray mass spectrometry (LC/MS), using a reverse phase C18 HPLC column in 0.1% trifluoroacetic acid and an increasing gradient of acetonitrile to elute the peptides. Brain extracts from similarly processed control mouse brains were also analyzed on LC/MS. The amount of extract used for this analysis corresponded to 2 mouse brains. Approximately 5% of the liquid chromatography output was sent directly to the electrospray mass spectrometer, and the remainder was collected into tubes. Aliquots of the collected material were analyzed by Matrix Associated Laser Desorption Ionization Mass Spectrometry (MALDI-MS).

B. Results

Figure 1:
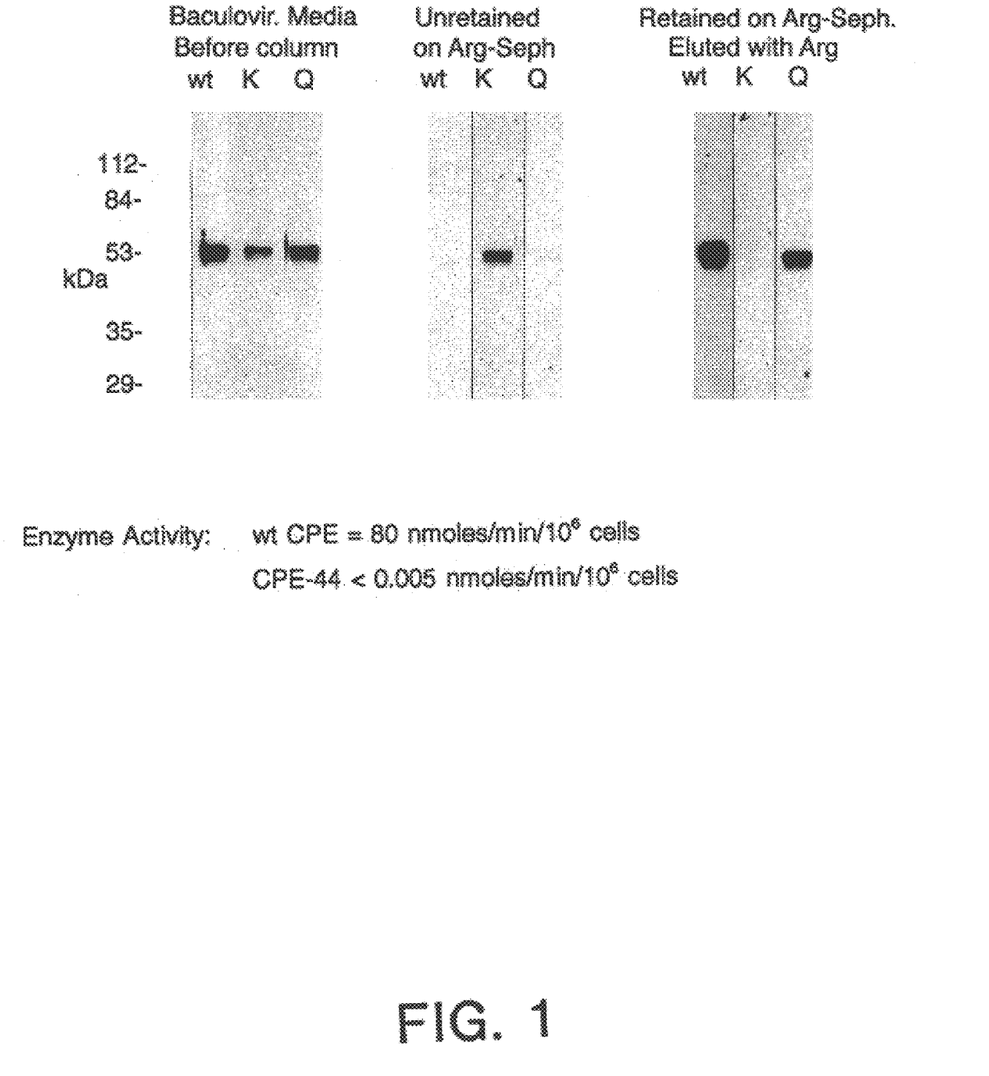

Wild type CPE is expressed in high levels in the baculovirus expression system, and is secreted into the media (see FIG. 1, left). CPE with $E^{342}$ mutated into either $K^{342}$ or $Q^{342}$ is also expressed and secreted from the baculovirus system (see FIG. 1, left). When the baculovirus media from the three CPE constructs was combined with an Arg-Sepharose resin, the $K^{342}$CPE W15 was not bound by this resin and remained in solution (FIG. 1, middle panel). In contrast, both wild type and the $Q^{342}$CPE were removed from solution by the Arg-Sepharose resin (FIG. 1, middle panel). When 25 mM Arg was added to the mixture, both wild type CPE and $Q^{342}$CPE were released from the resin (FIG. 1, right panel). This result indicates that the $Q^{342}$CPE mutant binds Arg, as does wild type CPE. Enzyme assays using dansyl-Phe-Ala-Arg could not detect any activity for the purified $Q^{342}$CPE, indicating that the mutation of $E^{342}$ into $Q^{342}$ reduced enzyme activity to less than 0.006% of the control activity.

To demonstrate that the $Q^{342}$CPE can be used to extract substrates for CPE from a solution, both wild type (wt) CPE and $Q^{343}$CPE were immobilized on Affigel-15. When the wt CPE resin was incubated with 100 nmoles of the CPE substrate (dansyl-Phe-Ala-Arg), greater than 99.9% of the material was recovered in the unbound fraction, and greater than 99% of this material was converted to product (dansyl-Phe-Ala), as determined from the solubility in chloroform (see Table 1). In contrast, when the same amount of peptide was incubated with the $Q^{342}$CPE resin, only 89.4 nmoles of the peptide were recovered in the unbound fractions, and less than 0.1% of this was converted into chloroform soluble products such as dansyl-Phe-Ala (Table 1).

Table 1 sets forth the results of the extraction of dansyl-Phe-Ala-Arg by immobilized CPE resin. The peptide (100 nmoles) was incubated with immobilized CPE in 3 ml of 0.1 M NaAc pH 5.5 buffer containing 1 M NaCl and 1% Triton X-100 for 16 hrs at 4° C. Then, the unbound material was recovered by filtration, and the resin was washed with 3 ml of the same buffer. The amount of unbound peptide was determined by measuring fluorescence (excitation 350 nm, emission 500 nm). The amount of peptide extracted by the resin was calculated as the difference between the amount applied (100 nmoles) and the amount recovered in the wash fraction. The % of peptide converted to dansyl-Phe-Ala was determined by extracting the material with chloroform and measuring the fluorescence of this organic phase.

TABLE 1

Extraction of dansyl-Phe-Ala-Arg by immobilized CPE resin

| Resin | nmoles peptide not bound to resin | nmoles peptide extracted by resin | % of peptide converted to dansyl-Phe-Ala |
|---|---|---|---|
| wt CPE | >99.9 | <0.1 | >99% |
| $Q^{342}$ CPE | 89.4 | 10.6 | <0.1 |

To demonstrate that bound CPE substrate could be recovered from the immobilized $Q^{342}$CPE resin, 5 nmoles of dansyl-Phe-Ala-Arg were applied to the resin, the columns were washed with buffer containing high salt and detergent, rinsed with low salt buffer, and then eluted with 25 mM Arg. For this analysis, the CPE inhibitor $HgCl_2$ was included in the incubation buffer. When wt CPE resin was used, nearly all of the 5 nmoles of peptide was recovered in the high salt/detergent wash (see Table 2). Only 69 pmoles of peptide was recovered in the elute fraction from the wt CPE resin (Table 2). In contrast, when the $Q^{342}$CPE resin was used, 2.1 nmoles of peptide were recovered in the high salt/detergent wash, and 200 pmoles of peptide were recovered in the elute fraction (Table 2).

Table 2 sets forth the results of the purification of dansyl-Phe-Ala-Arg by immobilized CPE resin. The peptide (5 nmoles) was applied to a 0.4 ml column containing the immobilized Q342 CPE (0.1 mg) on Affigel 15, in 0.1 M NaAc pH 5.5 buffer containing 0.01% Triton X-100 and 1 mM $HgCl_2$. The column flow through was re-applied to the column twice, and then the column was washed with 3 ml of 0.1 M NaAc pH 5.5 containing 1 M NaCl and 1% Triton X-100. The column was rinsed with 3 ml of 10 mM NaAc, pH 5.5, and eluted with 3 ml of 20 mM Tris pH 8.0 containing 0.01% Triton X-100 and 25 mM Arg. The amount of peptide in each fraction was determined by measuring the fluorescence (excitation 338 nm, emission 558 nm).

TABLE 2

Purification of dansyl-Phe-Ala-Arg by immobilized CPE resin

| Resin | peptide in wash | peptide in rinse | peptide in elute |
|---|---|---|---|
| wt CPE | >4.9 nmoles | <10 pmoles | 69 pmoles |
| $Q^{342}$ CPE | 2.1 nmoles | <10 pmoles | 200 pmoles |

To demonstrate that another immobilized enzyme can also bind a CPE substrate, 100 nmoles of dansyl-Phe-Ala-Arg were applied to 0.3 ml of anhydrotrypsin agarose (Takara Biomedicals). After washing the column with 20 ml of buffer, 66 nmoles were recovered in the unbound fractions. The remaining 34 nmoles of peptide were recovered when the columns were eluted with 5 mM HCl. This result indicates that the anhydrotrypsin agarose can also bind a CPE substrate, and this affinity column procedure is therefore not limited to mutant forms of CPE that bind substrates.

To demonstrate that immobilized enzyme that binds the CPE substrate dansyl-Phe-Ala-Arg also binds endogenous substrates present in the $Cpe^{fat}/Cpe^{fat}$ mouse tissue, brains from 3 mice were extracted in acetic acid, filtered through a microfiltration device to remove material greater than 10 kDa, and then applied to the anhydrotrypsin agarose. Brains from 3 non-fat littermates were similarly processed. The endogenous peptide Enk (Tyr-Gly-Gly-Phe-Leu) was measured by RIA. This RIA does not detect Arg-extended Enk (Tyr-Gly-Gly-Phe-Leu-Arg or Tyr-Gly-Gly-Phe-Leu-Arg-Arg), which are the endogenous CPE substrates. To measure these compounds, the brain extract was first digested with carboxypeptidase B (CPB), which removes the C-terminal Arg residues and generates Enk. The amount of C-terminally extended Enk was calculated from the increase in immunoreactive Enk caused by the CPB treatment. Control mouse brains contain 8.2 pmoles of immunoreactive Enk per brain, and this material does not bind to the anhydrotrypsin agarose column (Table 3). Brains from $Cpe^{fat}/Cpe^{fat}$ mice contain much less immunoreactive Enk (0.63 pmoles/brain) and this material also does not bind to the anhydrotrypsin column (Table 3). No Arg-extended Enk was detected in the fraction which did not bind to the column for either control or $Cpe^{fat}/Cpe^{fat}$ mouse brain (Table 3). Similarly, no immunoreactive Enk could be detected in the elute from the columns for either control or $Cpe^{fat}/Cpe^{fat}$ brains (Table 3). However, C-terminally extended Enk was detected in the elute fractions, with 0.02 pmoles detected in control brains, and 0.88 pmoles detected in $Cpe^{fat}/Cpe^{fat}$ brains (Table 3). This result indicates that the anhydrotrypsin agarose can purify an endogenous CPE substrate (i.e. Arg-extended Enk) from mouse brain. Furthermore, these data show that fully processed Enk is 13-fold lower, and the Arg-extended Enk is 44-fold higher in the $Cpe^{fat}/Cpe^{fat}$ mouse brain compared to the control mouse brain. The substantial increase in Arg-extended peptides in $Cpe^{fat}/Cpe^{fat}$ mice, and the affinity column technique to isolate these peptides are the first two parts of this novel technique.

Table 3 sets forth the results of an affinity column purification of endogenous enkephalin-containing peptides. Brains from $Cpe^{fat}/Cpe^{fat}$ mice or from control littermates were extracted in boiling 0.1 M acetic acid, filtered through a Centricon 10 microfiltration apparatus (Amincon), and applied to 0.3 ml of anhydrotrypsin agarose. The material not bound to the resin was saved for analysis. The columns were washed with 50 ml of buffer, and then eluted with 5 mM HCl. Aliquots of the material not bound to the column, and of the elute fraction, were either assayed directly without CPB (to detect Enk) or after digestion with carboxypeptidase B for 2 hours. The amount of Enk was measured using a RIA kit (Peninsula Laboratories); units are adjusted to pmoles per brain. Enk: the amount of immunoreactivity detected without CPB treatment. Enk-Arg: the increase in immunoreactivity resulting from the CPB treatment, due to the processing of either Enk-$Arg^6$ or Enk-$Arg^6$-$Arg^7$ to Enk.

TABLE 3

Affinity column purification of endogenous enkephalin-containing peptides.

| Brain extracts | Not bound to column | | Recovered in elute | |
|---|---|---|---|---|
| | Enk | Enk-Arg | Enk | Enk-Arg |
| Control Mice | 8.2 | <0.01 | <0.01 | 0.02 |
| $Cpe^{fat}/Cpe^{fat}$ mice | 0.63 | <0.01 | <0.01 | 0.88 |

To demonstrate that additional peptides are present in the affinity column elute fraction, and that these peptides are elevated in the Cpe$^{fat}$/Cpe$^{fat}$ mice compared to the control mice, the material was subjected to LC/MS using a gradient of acetonitrile over 80 minutes.

Figure 2A:
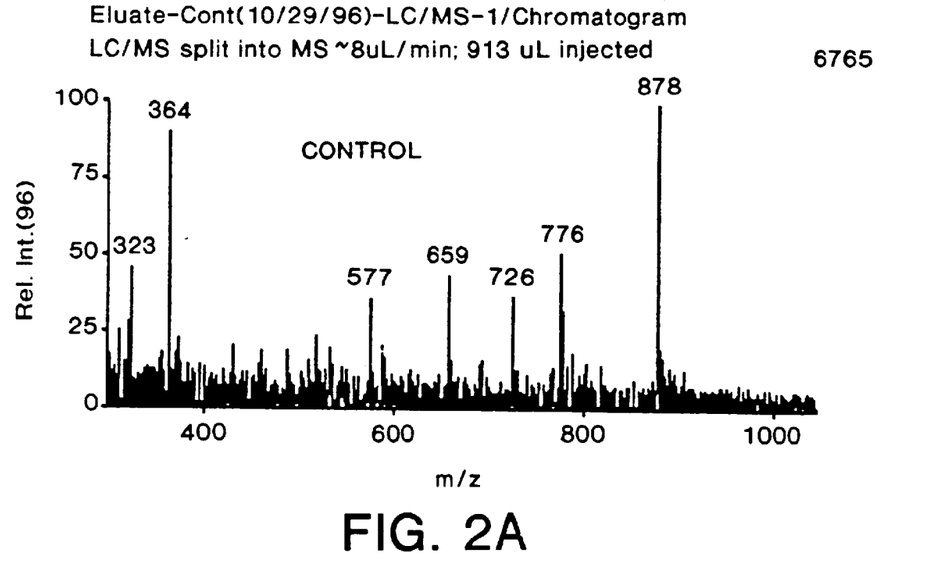
Figure 2B:
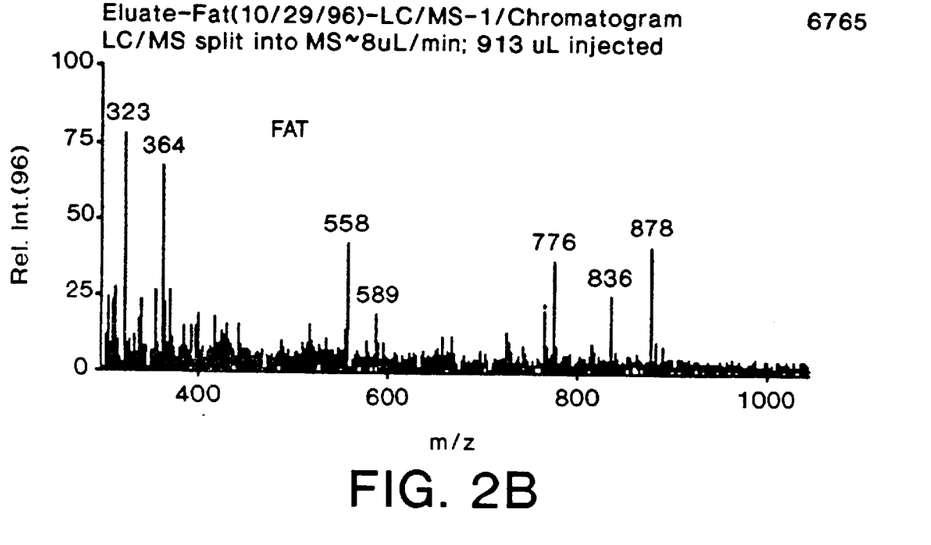
Figure 3A:
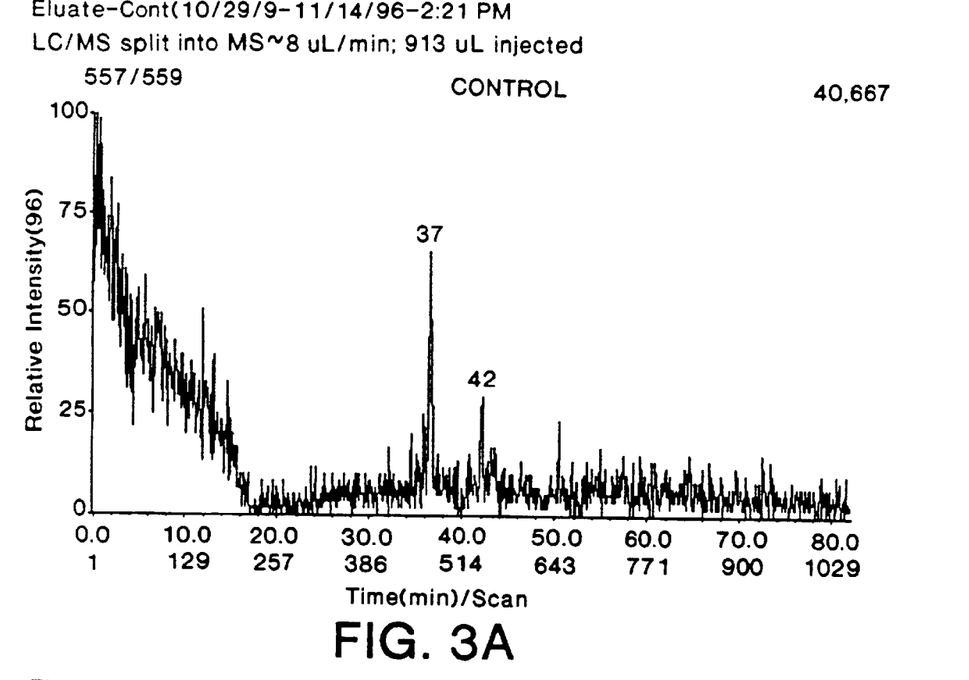
FIG. 3 sets forth the relative intensity of all ions with a m/z of 558±1 Da for each of the 1029 scans of the LC/MS of affinity purified material from control (top) and $Cpe^{fat}/Cpe^{fat}$ (bottom) mouse brains.
Figure 3B:
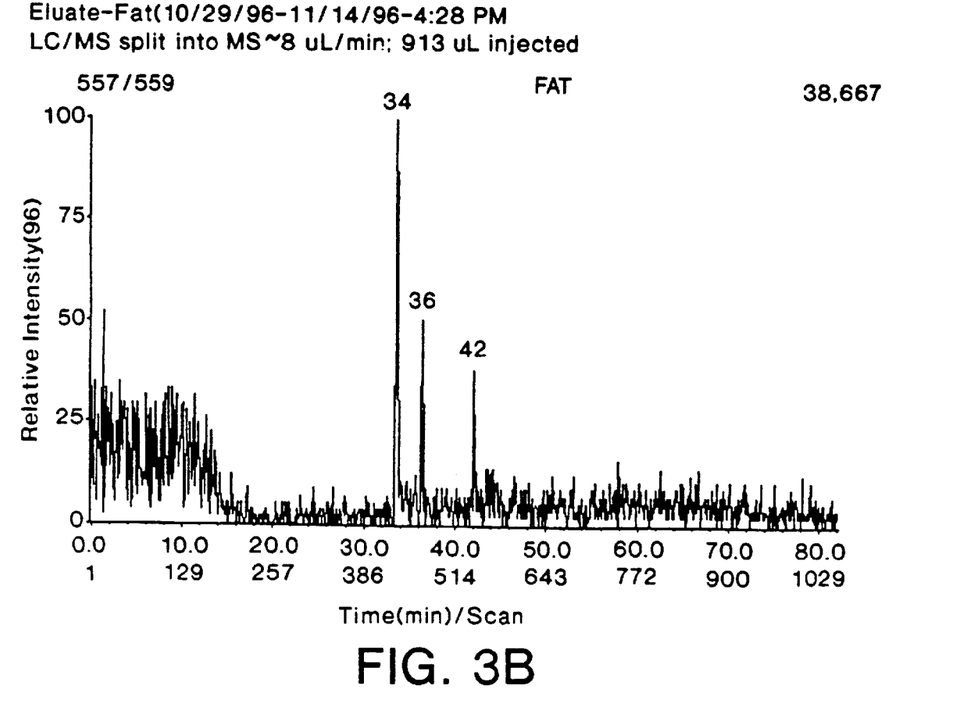
Figure 4A:
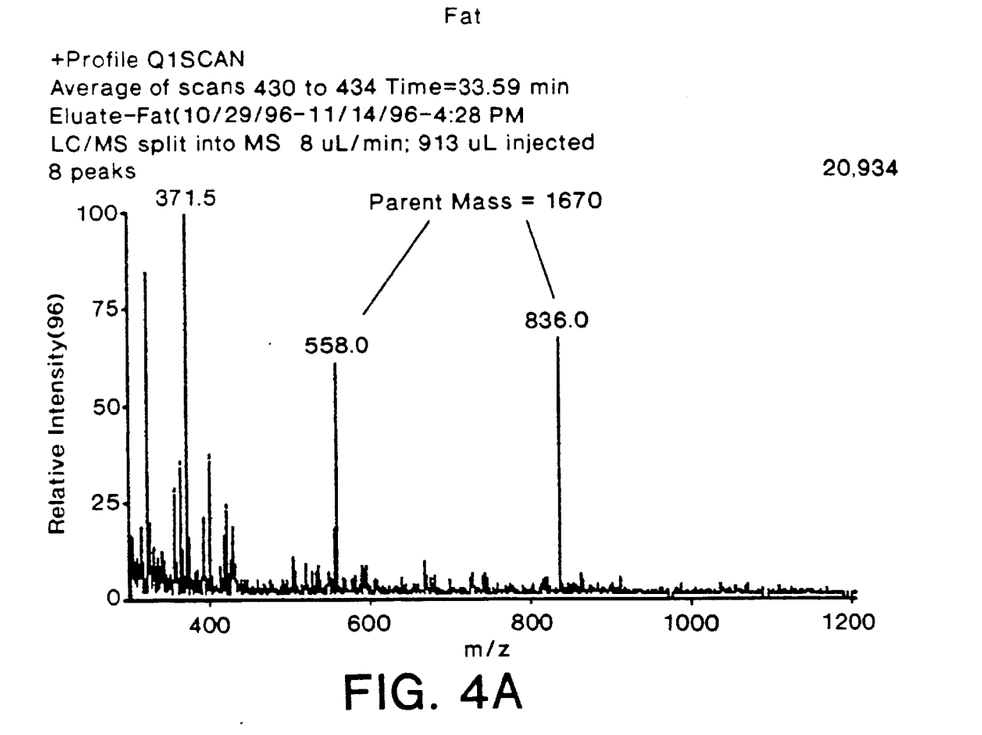
FIG. 4 sets forth the identification of a 1670±1 Da peptide in the affinity purified material from $Cpe^{fat}/Cpe^{fat}$ mouse brains that elutes from the LC around 33–34 minutes. Top: The average of scans 430–434, corresponding to the peak of the 558 ion (33.6 to 40 minutes). Bottom: Aliquots of the collected material corresponding to 33–34 minutes were analyzed by Matrix Associated Laser Desorption Ionization Mass Spectrometry (MALDI-MS).
Figure 4B:
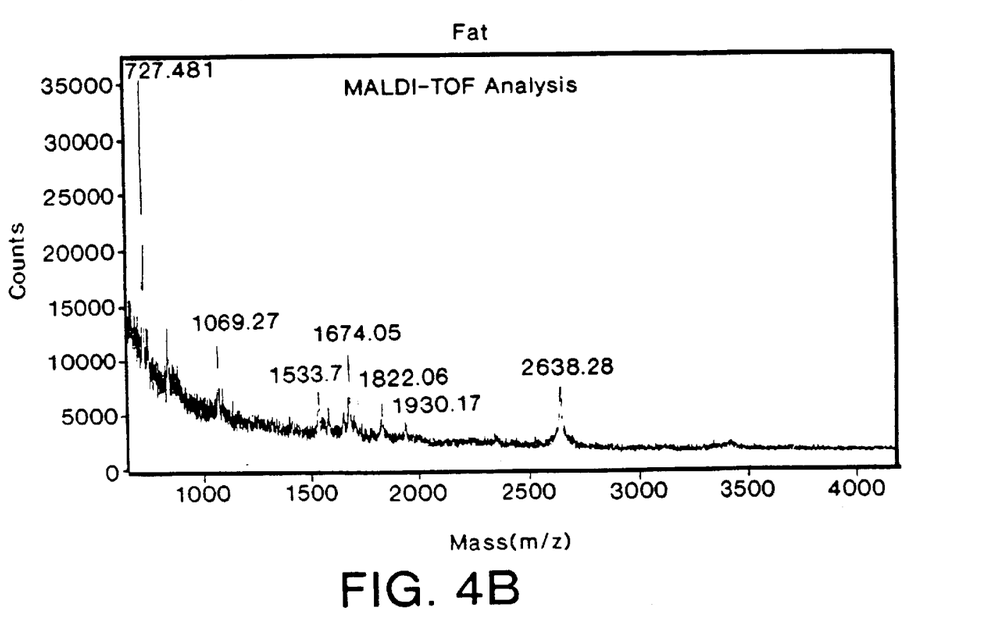

Analysis of the mass to charge (m/z) for the MS scans shows a number of ions that are more abundant in the Cpe$^{fat}$/Cpe$^{fat}$ than the control brain extracts. FIG. 2 shows the m/z for scans from 32 to 34 minutes; these results are representative, and many additional peaks are detected throughout the gradient. The Cpe$^{fat}$/Cpe$^{fat}$ extract shows increased signals for m/z of 341, 355, 400, 558, 766, and 836, compared to the corresponding scans of the control extracts (FIG. 2). To find the exact fractions in which each mass eluted from the LC column, each of the 1029 scans collected over the 80 minute gradient was searched for m/z within 1 mass unit of the mass detected in FIG. 2. A representative result is shown in FIG. 3, for m/z of 558±1. The extract from Cpe$^{fat}$/Cpe$^{fat}$ brain shows a major peak of 558±-1 eluting at 33.8 minutes, and minor peaks eluting at 37 and 42 minutes (FIG. 3, bottom). The control extract shows the 37 and 42 minute peaks, but not the major 34 minute peak (FIG. 3, top). This analysis confirms that the 558 ion is greatly elevated in the Cpe$^{fat}$/Cpe$^{fat}$ brain, compared to the control brain. Similar analysis for the other ions detected in the initial analysis of 2 minute intervals shows many of them to be greatly enriched in the Cpe$^{fat}$/Cpe$^{fat}$ brain compared to the control brain (not shown). One of the other ions, m/z=836, elutes at the same time as the 558 ion. The average of scans 430–434, which corresponds to the peak of 558 ion in FIG. 3, contains a strong signal for the 836 ion (FIG. 4, top). Thus, it is likely that these two ions represent the same peptide under different ionization states. The data are consistent with a parent mass of 1670±1, with the 836 ion representing the 2H$^+$form, and the 558 ion representing the 3H$^+$form.

To demonstrate that a 1670 Da peptide is present in the Cpe$^{fat}$/Cpe$^{fat}$ extracts, and that this peptide elutes from the LC around 34 minutes, fractions of the LC column were collected over 1 minute intervals. Each fraction was analyzed by MALDI-MS, which has a slightly reduced accuracy than the electrospray MS used for LC/MS, but is less prone to multiple ionizations. The fraction corresponding to the 33–34 minute eluate from the LC column shows a signal of mass 1673±5 Da (FIG. 4, bottom). Similar analysis of the control extracts does not show a mass in this range. These results show that a peptide of approximately 1673 Da is more abundant in the Cpe$^{fat}$/Cpe$^{fat}$ brain than in the control brain, and this peptide presumably corresponds to the 1670±1 Da peptide found in the LC/MS analysis. Similar analysis of other peaks detected in the LC/MS shows a large number of peptides to be elevated in the Cpe$^{fat}$/Cpe$^{fat}$ brain compared to control brain.

C. Discussion

Previous studies have shown that Cpe$^{fat}$/Cpe$^{fat}$ mice are defective in CPE due to a point mutation that inactivates the enzyme (Naggart, et al., (1995) *Nature Genetics*, 10: 135–142). Without active CPE, peptides are not properly processed in the Cpe$^{fat}$/Cpe$^{fat}$ mice (Naggart, et al., (1995) *Nature Genetics*, 10:135–142; Fricker, et al. (1996) *J. Biol. Chem* 271:30619–30624). Most importantly, peptides with C-terminal Lys and/or Arg residues (i.e. CPE substrates) accumulate to relatively high levels. Normally, these Lys and/or Arg extended peptides are at trace levels in brain and other tissues, and their accumulation in the Cpe$^{fat}$/Cpe$^{fat}$ mouse is the basis for their purification and identification.

Purification of the CPE substrates is readily accomplished using an affinity column consisting of modified enzyme attached to a solid support. Several affinity columns have been tested, and appear to be suitable for this purification. Mutation of a critical active site residue in CPE (E$^{342}$) to a Q causes the enzyme to be inactive, but still bind substrate. This mutant enzyme is therefore able to isolate CPE substrates from Cpe$^{fat}$/Cpe$^{fat}$ mouse brain. In addition, wild type CPE can also be used in the presence of a thiol-directed inhibitor such as mercuric chloride (HgCl2) or p-chloromercuriphenyl sulfonate. These inhibitors prevent CPE from cleaving substrates, but do not interfere with the binding of the substrates. The chelation of the active site metal from CPE may also inactivate the enzyme without affecting the ability of the enzyme to bind substrates; this approach has previously been used with carboxypeptidase B (Yasuhara and Ohasi (1990) *Biochem. Biophys. Res. Comm.* 166:330–335). Another approach is to chemically modify an enzyme so that it binds, but does not cleave CPE substrates. An example of this is anhydrotrypsin, which binds peptides with C-terminal basic residues but is enzymatically active. Anhydrotrypsin agarose is functionally similar to the CPE affinity columns, and all of these resins are able to isolate CPE substrates. Thus, the method of the present invention is not limited to a single affinity column type, but is a general procedure that can be used to purify endogenous CPE substrates from Cpe$^{fat}$/Cpe$^{fat}$ mouse tissues.

Based on the broad distribution of CPE in many neuroendocrine cells, it is likely that CPE processes a large number of bioactive peptides in a variety of tissues. The defect of CPE in the Cpe$^{fat}$/Cpe$^{fat}$ mouse will therefore lead to the accumulation of many CPE substrates, and not just the few peptides that have previously been examined. The data set forth herein using LC/MS to analyze the peptides isolated by affinity chromatography from Cpe$^{fat}$/Cpe$^{fat}$ mouse brain supports the idea that a large number of peptides are altered in these mice. It is anticipated that there are many undiscovered peptides in brain and other tissues, and the method described herein enables the identification of a great number of these. Several of the peptides identified in the Cpe$^{fat}$/Cpe$^{fat}$ mouse brain have been partially sequenced by tandem MS, and do not appear to correspond to known peptides.

The general approach of using a non-human model with a defect in an enzyme as a source to isolate the enzyme's substrates, together with an affinity column technique to purify these substrates, should be applicable to many other systems. For example, other peptide processing enzymes (prohormone convertase, amidation enzymes, etc.) could be used in a similar scheme to identify novel peptides. Furthermore, this approach is not limited to bioactive peptides, but could also be used to identify novel substrates for a variety of enzymes.

What is claimed is:

1. A method of identifying a substrate comprising the steps of:
   (a) obtaining an extract of a non-human model, wherein said extract contains at least one substrate that binds to carboxypeptidase E and said non-human model has an inactive version of carboxypeptidase E resulting in accumulation of said substrate in said non-human model;
   (b) fractionating said extract on an affinity resin column, wherein the affinity resin of the column comprises a protein bound to a solid support, and wherein said protein is selected from the group consisting of anhydrotrypsin, inactive carboxypeptidase E having a point mutation in the amino acid sequence of carboxypeptidase E of Glu$^{342}$ to Gln$^{342}$, and carboxypeptidase E used in the presence of a thiol-directed inhibitor (c) obtaining an elute fraction containing said substrate from said affinity column; and (d) purifying and identifying said substrate contained in said elute fraction.

2. The method of claim 1, wherein the inactive version of carboxypeptidase E resulting in accumulation of said substrate in said non-human model is caused by a mutation or a chemical modification of carboxypeptidase E.

3. The method of claim 2 wherein the inactive version of carboxypeptidase E resulting in accumulation of said substrate in said non-human model is caused by a mutation of carboxypeptidase E.

4. The method of claim 3 wherein the inactive version of carboxypeptidase E resulting in accumulation of said substrate in said non-human model is created by a point mutation in the amino acid sequence of carboxypeptidase E of $Ser^{202}$ to $Pro^{202}$ or $Ser^{202}$ to $Phe^{202}$.

5. The method of claim 1 wherein the non-human model is a prokaryote and the prokaryote is a bacterium.

6. The method of claim 1 wherein the non-human model is a eukaryote and the eukaryote is selected from the group consisting of a drosophila, fish, duck, mouse, rat, hamster, rabbit and pig.

7. The method of claim 6 wherein the non-human model is a mouse.

8. The method of claim 7 wherein the mouse is a $Cpe^{fat}/Cpe^{fat}$ mouse.

9. The method of claim 1 wherein the extract is selected from the group consisting of cell or tissue extracts from brain, testis, heart, duodenum, ovary, skeletal muscle, lung, liver, kidney, spleen, thymus, stomach, veins, arteries, glands, colon, pancreas, and intestine.

10. The method of claim 1 wherein the thiol-directed inhibitor is mercuric chloride or p-chloromercuriphenyl.

* * * * *